(12) United States Patent
Okamoto et al.

(10) Patent No.: US 9,939,387 B2
(45) Date of Patent: Apr. 10, 2018

(54) OPTICAL INSPECTION DEVICE

(71) Applicant: Ishida Co., Ltd., Kyoto (JP)

(72) Inventors: Tsutomu Okamoto, Ritto (JP); Emi Mizuno, Ritto (JP); Yoshinori Tarumoto, Ritto (JP)

(73) Assignee: Ishida Co., Ltd., Kyoto (JP)

( * ) Notice: Subject to any disclaimer, the term of this patent is extended or adjusted under 35 U.S.C. 154(b) by 0 days.

(21) Appl. No.: 15/102,725

(22) PCT Filed: Nov. 11, 2014

(86) PCT No.: PCT/JP2014/079865
§ 371 (c)(1),
(2) Date: Jun. 8, 2016

(87) PCT Pub. No.: WO2015/087653
PCT Pub. Date: Jun. 18, 2015

(65) Prior Publication Data
US 2017/0023488 A1    Jan. 26, 2017

(30) Foreign Application Priority Data
Dec. 13, 2013  (JP) .................. 2013-258319

(51) Int. Cl.
*G01N 21/88*    (2006.01)
*G01N 21/59*    (2006.01)
(Continued)

(52) U.S. Cl.
CPC ......... *G01N 21/8806* (2013.01); *G01N 21/59* (2013.01); *G01N 21/90* (2013.01);
(Continued)

(58) Field of Classification Search
CPC ...... G01N 21/90; G01N 21/94; G01N 21/359; G01N 21/59; G01N 21/8806;
(Continued)

(56) References Cited

U.S. PATENT DOCUMENTS 4,031,752 A    6/1977  Sanders
4,707,138 A    11/1987 Coatney
(Continued)

FOREIGN PATENT DOCUMENTS

JP    2003-197699 A    7/2003
JP    2004-157027 A    6/2004
(Continued)

OTHER PUBLICATIONS

International Search Report; PCT/JP2014/079865 dated Dec. 16, 2014.
(Continued)

*Primary Examiner* — David Porta
*Assistant Examiner* — Blake Riddick
(74) *Attorney, Agent, or Firm* — Studebaker & Brackett PC

(57) ABSTRACT

An optical inspection apparatus 1 includes a light radiation unit 11 configured to radiate light to an article 50, a light detection unit 12 configured to detect transmitted light of the light radiated to the article 50, and a support unit 13 configured to support the light radiation unit 11 and the light detection unit 12 in a cantilever manner. An inspection region of the article 50 by the light is exposed to an ambient atmosphere.

6 Claims, 6 Drawing Sheets

(51) Int. Cl.
*G01N 21/90* (2006.01)
*G01N 21/94* (2006.01)
*G01N 21/95* (2006.01)
*G01N 21/84* (2006.01)
*G01N 21/89* (2006.01)

(52) U.S. Cl.
CPC ............. *G01N 21/94* (2013.01); *G01N 21/95* (2013.01); *G01N 21/8901* (2013.01); *G01N 2021/845* (2013.01); *G01N 2201/062* (2013.01)

(58) Field of Classification Search
CPC ............... G01N 21/8901; G01N 21/95; G01N 2021/845; G01N 2201/062
USPC .......................................... 250/338.1, 339.06
See application file for complete search history.

(56) References Cited

U.S. PATENT DOCUMENTS

| | | | | |
|---|---|---|---|---|
| 4,995,531 A * | 2/1991 | Summers | ................ | B29D 30/32 198/467.1 |
| 5,168,224 A * | 12/1992 | Maruizumi | ............ | G01N 23/04 324/300 |
| 5,917,602 A * | 6/1999 | Bonewitz | ............. | G01B 11/022 348/127 |
| 6,384,421 B1 | 5/2002 | Gochar, Jr. | | |
| 6,610,953 B1 * | 8/2003 | Tao | .......... | B07C 5/342 209/11 |
| 6,753,527 B1 * | 6/2004 | Yamagishi | .......... | G01F 23/2921 250/223 B |
| 6,914,678 B1 * | 7/2005 | Ulrichsen | ................ | B07C 5/342 356/429 |
| 2005/0188859 A1 * | 9/2005 | Bruce, III | ............ | G01N 21/359 99/486 |
| 2006/0030060 A1 * | 2/2006 | Noguchi | ................ | B82Y 15/00 438/14 |
| 2007/0164194 A1 * | 7/2007 | Kurata | ................. | G02B 21/247 250/201.4 |
| 2008/0024773 A1 * | 1/2008 | Miyazaki | ........... | G01N 21/4738 356/237.2 |
| 2008/0031411 A1 * | 2/2008 | Klingenbeck-Regn | ............................. | A61B 6/022 378/41 |
| 2010/0260378 A1 * | 10/2010 | Noy | ....................... | G01B 11/24 382/103 |
| 2011/0026673 A1 * | 2/2011 | Mastronardi | ........ | G01V 5/0008 378/57 |
| 2012/0287425 A1 * | 11/2012 | Ooyama | .............. | G01B 11/306 356/237.1 |
| 2013/0222806 A1 * | 8/2013 | Klokkerud | ........... | G01N 21/278 356/446 |
| 2014/0174127 A1 * | 6/2014 | Dalstra | .................. | G01N 25/72 65/29.11 |
| 2015/0241341 A1 * | 8/2015 | Ikeda | ..................... | G01N 23/10 250/338.1 |
| 2015/0276605 A1 * | 10/2015 | Kawamuki | ........ | G01N 21/6456 250/458.1 |
| 2016/0033404 A1 * | 2/2016 | Suzuki | ............... | G01N 21/3581 250/338.1 |
| 2016/0223705 A1 * | 8/2016 | Sugimoto | ............... | B65B 65/08 |

FOREIGN PATENT DOCUMENTS

JP      2008-076218 A      4/2008
JP      2012-189563 A      10/2012

OTHER PUBLICATIONS

Notification of Transmittal of Translation of the International Preliminary Report on Patentability and Translation of Written Opinion of the International Searching Authority; PCT/JP2014/079865 dated Jun. 23, 2016.

The extended European search report issued by the European Patent Office dated Jun. 19, 2017, which corresponds to European Patent Application No. 14869756.8-1504 and is related to U.S. Appl. No. 15/102,725.

* cited by examiner

OPTICAL INSPECTION DEVICE

TECHNICAL FIELD

The present invention relates to an optical inspection apparatus.

BACKGROUND ART

In a conveying line of an article in which contents such as food are packed in a package such as a film packaging material and are shipped, it is necessary to inspect a condition of the article to prevent a defected article (for example, the contents caught in a sealed portion of the package, the contents damaged in the package, a foreign matter mixed into the package, and the like) from being shipped.

As an apparatus for inspecting such condition of the article, for example, Patent Literature 1 discloses an optical inspection apparatus including an upstream conveying unit and a downstream conveying unit that convey an article, an illumination unit that emits light to the article from above a gap between the upstream conveying unit and the downstream conveying unit, and an imaging unit that images the article from below the gap.

CITATION LIST

Patent Literature

Patent Literature 1: Japanese Unexamined Patent Publication No. 2012-189563

SUMMARY OF INVENTION

Technical Problem

To install the optical inspection apparatus according to Patent Literature 1 in an existing conveying line conveying an article, however, a space equivalent to the upstream conveying unit and the downstream conveying unit is necessary in the existing conveying line. Thus, it is necessary to make a layout change and the like of the conveying line, which may be a complicated task.

Accordingly, an objective of the present invention is to provide an optical inspection apparatus that can be easily installed in the existing conveying line conveying an article.

Solution to Problem

An optical inspection apparatus according to one aspect of the present invention includes: a light radiation unit configured to radiate light to an article; a light detection unit configured to detect transmitted light of the light radiated to the article; and a support unit configured to support the light radiation unit and the light detection unit in a cantilever manner; and an inspection region of the article by the light is exposed to an ambient atmosphere.

According to this optical inspection apparatus, the optical inspection apparatus can be easily installed in the existing conveying line conveying an article from one of sides of the conveying line such that a light radiation unit and a light detection unit face each other interposing a gap between successive conveyers. Note that as light to be radiated, for example, visible light, ultraviolet light, near infrared light, infrared light, and the like may be used.

In the optical inspection apparatus according to one aspect of the present invention, the light detection unit may be disposed upward relative to the light radiation unit. In this configuration, it is possible to suppress sticking of dust to the light detection unit that may more easily deteriorate detection accuracy than sticking of dust to the light radiation unit. It is also possible to suppress light such as of illumination around the optical inspection apparatus from entering the light detection unit as ambient light.

In the optical inspection apparatus according to one aspect of the present invention, the light radiation unit and the light detection unit may be vertically movable integrally with a support unit. In this configuration, it is possible to easily adjust positions of the light radiation unit and the light detection unit relative to the existing conveying line.

In the optical inspection apparatus according to one aspect of the present invention, the position of the light detection unit may also be adjustable relative to that of the light radiation unit. In this configuration, it is possible to accurately adjust the position of the light detection unit.

In the optical inspection apparatus according to one aspect of the present invention, the light radiation unit and the light detection unit may be rotatable integrally with the support unit. In this configuration, for example, in a case where a conveyance surface of the successive conveyers in the existing conveying line is tilted, it is possible to easily adjust angles of the light radiation unit and the light detection unit relative to the existing conveying line such that the light radiation unit and the light detection unit face each other in a direction perpendicular to the conveyance surface.

In the optical inspection apparatus according to one aspect of the present invention, the light radiation unit and the light detection unit may be rotatable integrally with the support unit about a position as a center, the position being at a shorter distance from the light radiation unit than a distance from the light detection unit. In this configuration, since a rotation amount of the light radiation unit is smaller than a rotation amount of the light detection unit, by disposing the light radiation unit in the vicinity of the gap between the successive conveyers, it is possible to suppress a reduction in detection sensitivity of the light detection unit caused by attenuation of the light to be radiated to the article.

In the optical inspection apparatus according to one aspect of the present invention, the support unit may include a pole unit, a first beam unit fixed to the pole unit at one end thereof and configured to support the light radiation unit, and a second beam unit fixed to the pole unit at one end thereof and configured to support the light detection unit. In this configuration, for example, compared to a case where the light radiation unit and the light detection unit are supported by a support unit having a curved shape, it is possible to dispose the light radiation unit and the light detection unit to desired positions while suppressing interference between the support unit and the existing conveying line.

In the optical inspection apparatus according to one aspect of the present invention, the light may be near infrared light. By using the near infrared light having higher transmissivity than visible light, it is possible to accurately inspect a condition of the article.

The optical inspection apparatus according to one aspect of the present invention may further include a control unit that acquires a light transmission image of the article having contents contained in a package from the light detection unit, sets an inspection region corresponding to a sealed portion of the package based on a positional relationship of the sealed portion saved in advance, and inspects the contents caught in the sealed portion with targeting the inspection region. In this configuration, it is possible to easily and securely set the inspection region corresponding to the sealed portion.

Advantageous Effects of Invention

According to the present invention, it is possible to provide an optical inspection apparatus that can be easily installed in the existing conveying line conveying an article.

DESCRIPTION OF EMBODIMENTS

Figure 1:
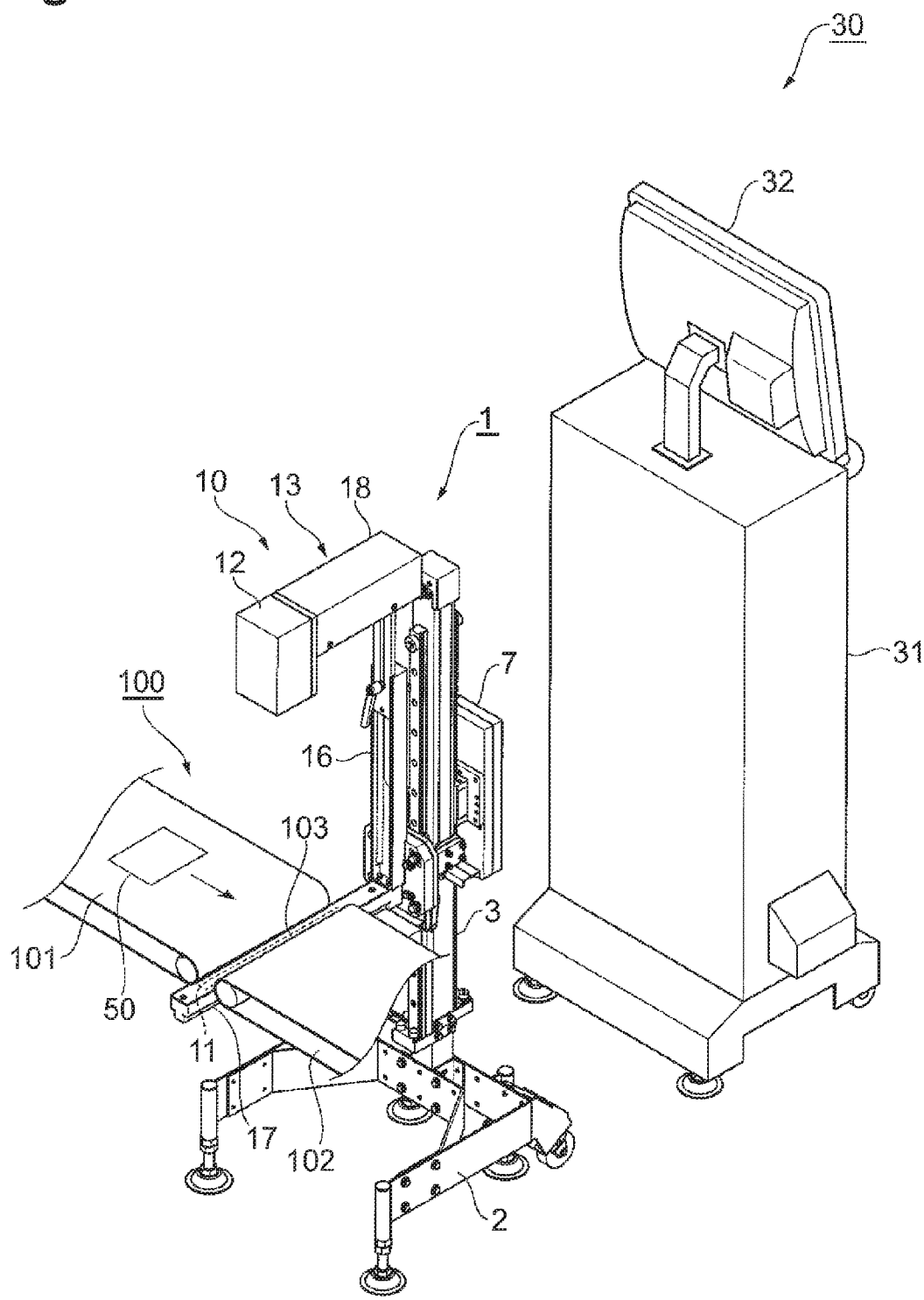
FIG. 1 is a perspective view illustrating an optical inspection system provided with an optical inspection apparatus according to one embodiment of the present invention.

Hereinafter, a preferred embodiment of the present invention is described in detail with reference to the drawings. Note that in each of the drawings, an identical or equivalent part is denoted by the same reference numeral, and a duplicated description thereof is omitted herein.

As illustrated in FIG. 1, an optical inspection apparatus 1 is an apparatus posteriorly installed in a part where there is a gap 103 between successive conveyers 101 and 102 in an existing conveying line 100 conveying an article 50. An object to be inspected by the optical inspection apparatus 1, for example, is the article 50 having a package such as of a film packaging material and contents such as food contained in the package. A control device 30 is electrically connected to the optical inspection apparatus 1 through a cable or by radio, and the optical inspection apparatus 1 and the control device 30 constitute an optical inspection system.

The control device 30 includes a control box 31 housing a computer, and an operation panel 32. The control device 30 controls operation of the optical inspection apparatus 1, finds any defect of the article 50 (for example, the contents caught in a sealed portion of the package, the contents damaged within the package, a foreign matter mixed into the package, and the like) based on a detection signal output from the optical inspection apparatus 1, and estimates volume (mass, quantity, and the like) of the contents in the package.

Figure 2:
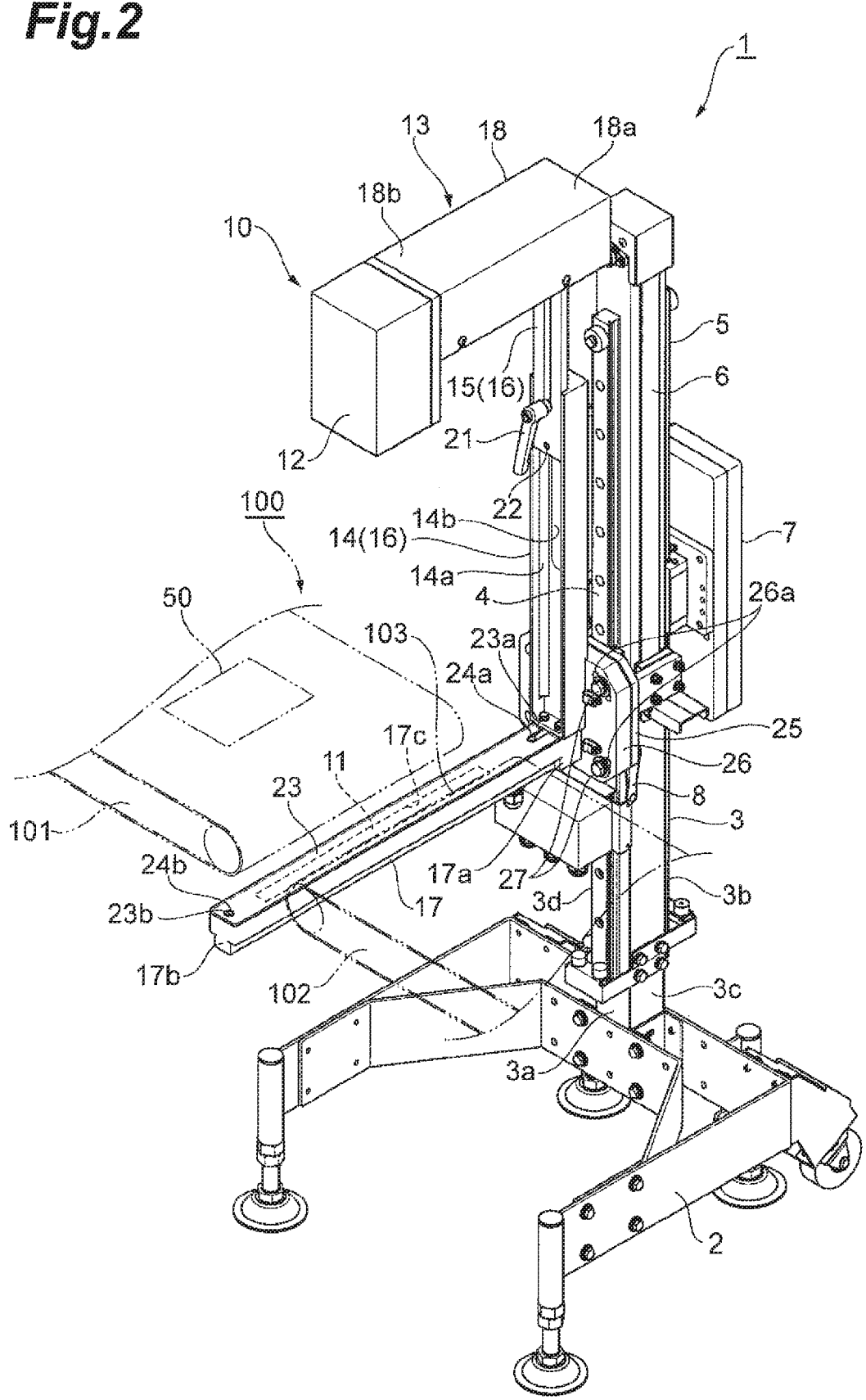
FIG. 2 is a perspective view illustrating the optical inspection apparatus of FIG. 1.

As illustrated in FIG. 2, the optical inspection apparatus 1 includes a leg unit 2 installed in a floor surface, and a quadrangular prism-shaped main pole 3 vertically disposed on the leg unit 2. A guide rail 4 extending in a vertical direction is provided to a front face 3a (a face on a conveying line 100 side) of the main pole 3. A guide rail 5 extending in the vertical direction is provided to a rear face 3b of the main pole 3. A belt 6 is stretched over a right side face 3c (a face on the right as viewed from the conveying line 100 side) and a left side face 3d of the main pole 3 through an upper end of the main pole 3.

An inspection head 10 is mounted on the guide rail 4 so as to be movable along the guide rail 4. One end of the belt 6 positioned on the right side face 3c of the main pole 3 is fixed to the inspection head 10. A weight 7 is mounted on the guide rail 5 so as to be movable along the guide rail 5. The other end of the belt 6 positioned on the left side face 3d of the main pole 3 is fixed to the weight 7.

Figure 3:
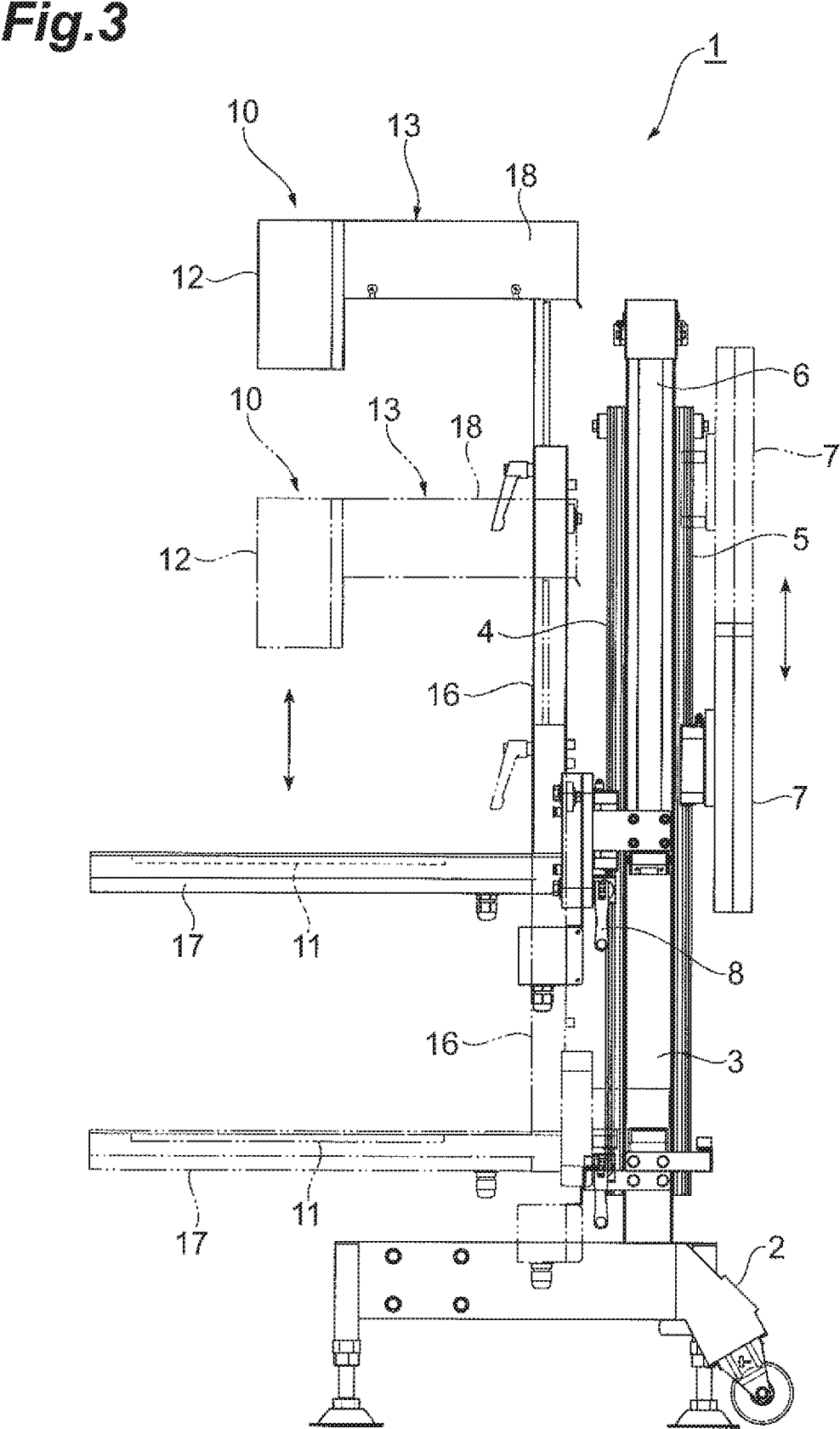
FIG. 3 is a right side view illustrating the optical inspection apparatus of FIG. 2.

In this configuration, as illustrated in FIG. 3, by moving the inspection head 10 up along the guide rail 4, the weight 7 is moved down along the guide rail 5. On the other hand, by moving the inspection head 10 down along the guide rail 4, the weight 7 is moved up along the guide rail 5. Once the inspection head 10 is disposed to a desired height, the inspection head 10 is fixed to the main pole 3 by a lever 8. In this way, by using the weight 7, a vertical movement of the inspection head 10 relative to the main pole 3 is made smooth in the optical inspection apparatus 1.

As illustrated in FIG. 2, the inspection head 10 includes: a light radiation unit 11 configured to radiate light to the article 50; a light detection unit 12 configured to detect transmitted light of the light radiated to the article 50; and a support unit 13 configured to support the light radiation unit 11 and the light detection unit 12 in a cantilever manner. The light radiation unit 11 is disposed below the gap 103 between the successive conveyers 101 and 102, and the light detection unit 12 is disposed above the gap 103. An optical path of the light from the light radiation unit 11 to the light detection unit 12 is exposed to an ambient atmosphere. That is, an inspection region of the article 50 by the light is exposed to the ambient atmosphere and is not covered with a shield box or the like. Note that a cover may be provided to shield ambient light so as to cover at least a part of the inspection region.

The light radiation unit 11 has a plurality of LEDs disposed along a horizontal direction (direction in which the gap 103 extends). At the time when the article 50 passes above the gap 103 between the successive conveyers 101 and 102, the light radiation unit 11 radiates near infrared light to the article 50 through the gap 103. Note that a wavelength of the near infrared light is from 780 nm to 1100 nm.

The light detection unit 12 is a line sensor and has a plurality of PDs disposed along the horizontal direction (direction in which the gap 103 extends). At the time when the article 50 passes above the gap 103 between the successive conveyers 101 and 102, the light detection unit 12 detects transmitted light of the near infrared light radiated to the article 50 and outputs a detection signal to the control device 30.

The support unit 13 includes: a pole unit 16 has a first pole part 14 and a second pole part 15; a first beam unit 17; and a second beam unit 18. The first pole part 14 is provided with a guide groove 14a extending in the vertical direction. The second pole part 15 is mounted on the guide groove 14a so as to be movable along the guide groove 14a. The first pole part 14 and the second pole part 15 are mutually fixed by a lever 21. A stopper bolt 22 having a cushion member is fixed to a lower end of the second pole part 15 through a long hole 14b formed in the first pole part 14. Accordingly, even in a case where the second pole part 15 is unintendedly dropped due to release of the lever 21, it is possible to stop dropping of the second pole part 15 while absorbing a shock.

One end 17a of the first beam unit 17 is fixed to a lower end of the first pole part 14, and another end 17b of the first beam unit 17 is a free end. The first beam unit 17 is provided with a recessed portion 17c opened upward, and the light radiation unit 11 is housed in the recessed portion 17c. That is, being supported by the first beam unit 17, the light radiation unit 11 is supported by the support unit 13 in the cantilever manner.

An opened portion of the recessed portion 17c is covered with a light transmitting cover 23 placed on the first beam unit 17. The cover 23 is formed by, for example, a light transmitting resin. In the cover 23, a cut-off 23a opened to an opposite side of the other end 17b of the first beam unit 17 is provided to a part corresponding to the one end 17a of the first beam unit 17. In the cover 23, a round hole 23b is provided to a part corresponding to the other end 17b of the first beam unit 17. The cover 23 is positioned in the first beam unit 17 by a pin 24a, which is vertically disposed on the one end 17a of the first beam unit 17, being fitted into the cut-off 23a as well as by a pin 24b, which is vertically disposed on the other end 17b of the first beam unit 17, being fitted into the round hole 23b. Note that each of the pins 24a and 24b is, for example, a head of a bolt.

One end 18a of the second beam unit 18 is fixed to an upper end of the second pole part 15, and another end 18b of the second beam unit 18 is a free end. The light detection unit 12 is mounted on the other end 18b, or the free end, of the second beam unit 18. That is, the light detection unit 12 is supported by the second beam unit 18, and thereby the light detection unit 12 is supported by the support unit 13 in the cantilever manner.

Figure 4:
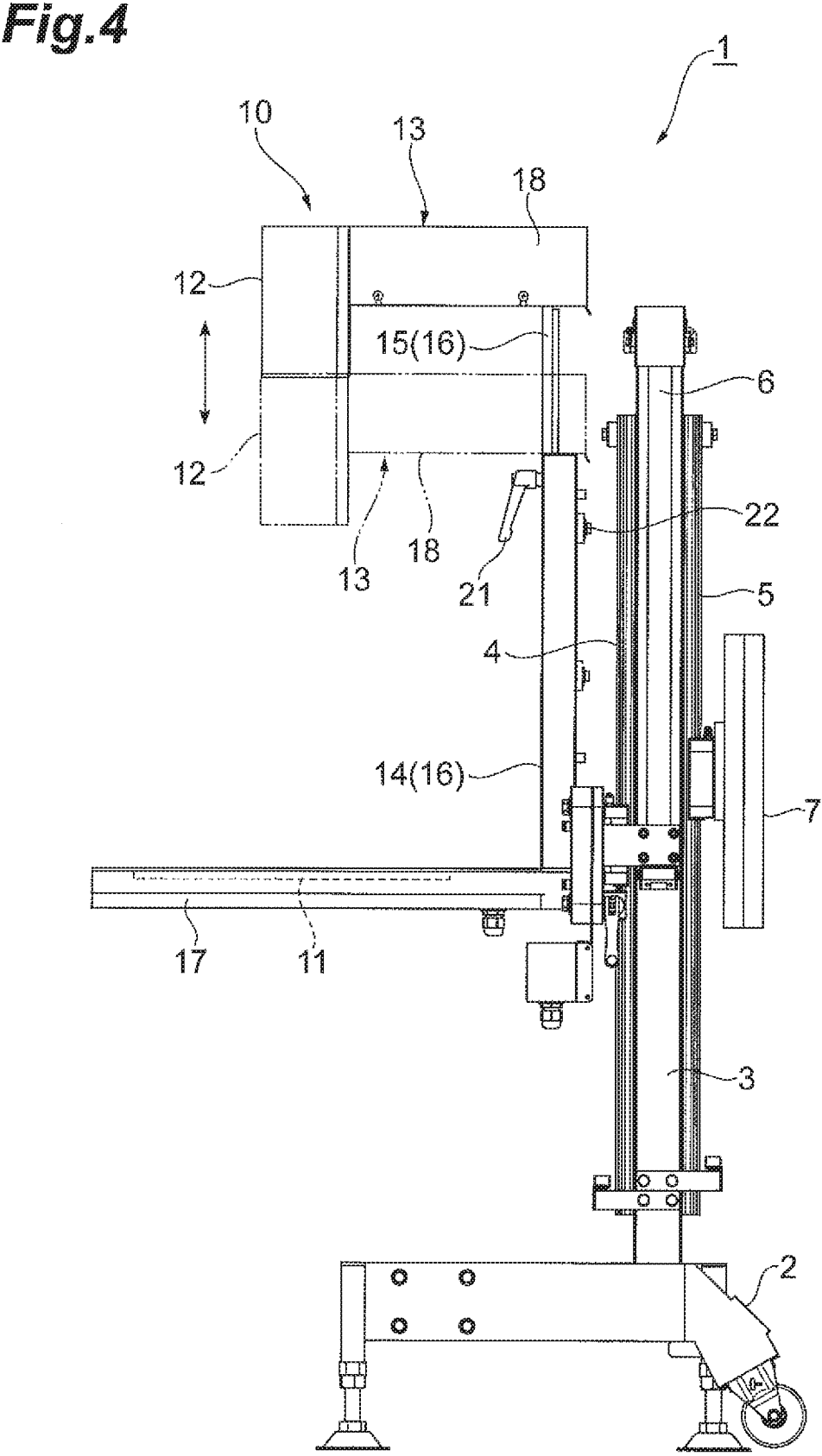
FIG. 4 is a right side view illustrating the optical inspection apparatus of FIG. 2.

In the above-described configuration of the support unit 13, as illustrated in FIG. 4, in a state where the lever 21 is released, the light detection unit 12 is moved up and down integrally with the second pole part 15 and the second beam unit 18. After the light detection unit 12 is disposed to a desired height, the light detection unit 12 is fixed relative to the light radiation unit 11 as a result of the first pole part 14 and the second pole part 15 being fixed to each other by the lever 21.

As illustrated in FIG. 2, a first plate 25 and a second plate 26 each having a rectangular plate shape are mounted on the lower end of the first pole part 14. The first plate 25 is mounted on the guide rail 4 so as to be movable along the guide rail 4. One end of the belt 6 positioned on the right side face 3c of the main pole 3 is fixed to the first plate 25. The second plate 26 is fixed to the first plate 25 by each of bolts 27 inserted into each of arc-shaped long holes 26a provided to each of four corners of the second plate 26. The lower end of the first pole part 14 is fixed to the second plate 26.

Figure 5:
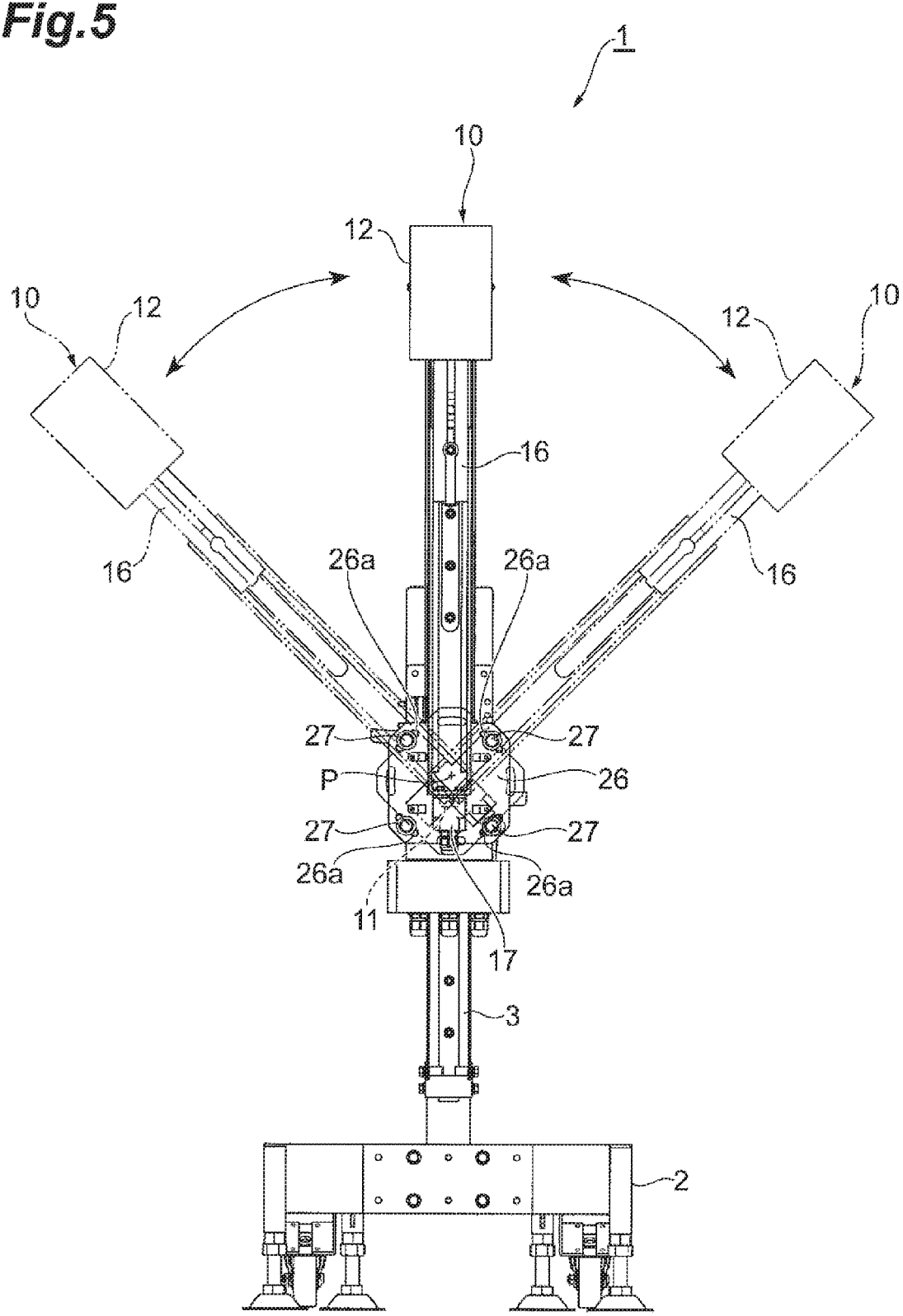
FIG. 5 is a front view illustrating the optical inspection apparatus of FIG. 2.

In this configuration, as illustrated in FIG. 5, in a state where the bolt 27 is loose, the inspection head 10 is rotated within a range of the arc-shaped long hole 26a. At this time, a position P to be a center of rotation of the inspection head 10 is center positions (center positions as viewed from the conveying line 100 side) of the first plate 25 and the second plate 26, which are mounted on the lower end of the first pole part 14. In this way, a distance from the light radiation unit 11 to the position P is shorter than a distance from the light detection unit 12 to the position P. After the inspection head 10 is disposed to a desired angle, the inspection head 10 is fixed relative to the main pole 3 as a result of tightening each of the bolts 27.

As described above, in the optical inspection apparatus 1, the light radiation unit 11 and the light detection unit 12 are supported by the support unit 13 in the cantilever manner, and the inspection region of the article 50 by the light is exposed to the ambient atmosphere. Thus, it is possible to easily install the optical inspection apparatus 1 in the existing conveying line 100 conveying the article 50 from one of sides of the conveying line 100 such that the light radiation unit 11 and the light detection unit 12 face each other interposing the gap 103 between the successive conveyers 101 and 102.

Furthermore, in the optical inspection apparatus 1, the light detection unit 12 is disposed upward relative to the light radiation unit 11. In this configuration, since the light detection unit 12 faces downward, it is possible to suppress sticking of dust to the light detection unit 12 that may more easily deteriorate detection accuracy than sticking of dust to the light radiation unit 11. It is also possible to suppress light such as illumination around the optical inspection apparatus 1 from entering the light detection unit 12 as ambient light. Moreover, it is possible to easily clean the light detection unit 12 in a large space above the existing conveying line 100.

In the optical inspection apparatus 1, the light radiation unit 11 disposed below the light detection unit 12 is covered with the light transmitting cover 23. In this configuration, in a case where dust sticks to the cover 23, it is possible to clean the cover 23 by detaching the cover 23 or to replace it with a new cover 23. In particular, in the first beam unit 17, since the cover 23 is positioned by the pin 24a being fitted into the cut-off 23a as well as by the pin 24b being fitted into the round hole 23b, even in a case where a space between the existing conveying line 100 and the first beam unit 17 is small, by sliding the cover 23 in the horizontal direction, it is possible to attach or detach the cover 23 to or from the first beam unit 17 without using a tool or the like. Note that the cover 23 may also have a lens function for concentrating light emitted from the light radiation unit 11 or a filter function for blocking light of a predetermined wavelength.

While a distance equivalent to a focal distance is necessary between a conveyance surface of the existing conveying line 100 and the light detection unit 12, it is preferred that a distance between the conveyance surface thereof and the light radiation unit 11 be small from a viewpoint of suppressing attenuation of light to be radiated to the article 50. Since the light detection unit 12 is disposed upward relative to the light radiation unit 11 in the optical inspection apparatus 1, it is possible to easily install the optical inspection apparatus 1 in the conveying line 100 even in a case where a height of the conveyance surface of the existing conveying line 100 is low.

In the optical inspection apparatus 1, the light radiation unit 11 and the light detection unit 12 is vertically movable integrally with the support unit 13. In this configuration, it is possible to easily adjust positions of the light radiation unit 11 and the light detection unit 12 relative to the existing conveying line 100.

In the optical inspection apparatus 1, the position of the light detection unit 12 is adjustable relative to that of the light radiation unit 11. In this configuration, it is possible to accurately adjust the position of the light detection unit 12 and to focus the light detection unit 12 on the article 50.

In the optical inspection apparatus 1, the light radiation unit 11 and the light detection unit 12 are rotatable integrally with the support unit 13. In this configuration, in a case where the conveyance surface of the successive conveyers 101 and 102 in the existing conveying line 100 is tilted, for example, it is possible to easily adjust angles of the light radiation unit 11 and the light detection unit 12 relative to the existing conveying line 100 such that the light radiation unit 11 and the light detection unit 12 face each other in a direction perpendicular to the conveyance surface.

In the optical inspection apparatus 1, the light radiation unit 11 and the light detection unit 12 are rotatable integrally with the support unit 13 about the position P, which is at a shorter distance from the light radiation unit 11 than that from the light detection unit 12, as a center. In this configuration, since a rotation amount of the light radiation unit 11 is smaller than a rotation amount of the light detection unit 12, by disposing the light radiation unit 11 in the vicinity of the gap 103 between the successive conveyers 101 and 102, it is possible to suppress a reduction in detection sensitivity of the light detection unit 12 caused by the attenuation of the light to be radiated to the article 50. Furthermore, the rotation amount of the light radiation unit 11, which is positioned in a space below the existing conveying line 100, is smaller than the rotation amount of the light detection unit 12, which is positioned in a space above the existing conveying line 100. Thus, it is possible to suppress interference between the light radiation unit 11 and any member of the conveying line 100 within the small space below the existing conveying line 100.

In the optical inspection apparatus 1, the support unit 13 includes: the pole unit 16; the first beam unit 17 fixed to the pole unit 16 at the one end 17a thereof; and the second beam unit 18 fixed to the pole unit 16 at the one end 18a thereof. The first beam unit 17 supports the light radiation unit 11, and the second beam unit 18 supports the light detection unit 12. In this configuration, compared to a case where the light radiation unit 11 and the light detection unit 12 are supported by a support unit having a curved shape, for example, it is possible to dispose the light radiation unit 11 and the light detection unit 12 to desired positions while suppressing interference between the support unit 13 and the existing conveying line 100.

In the optical inspection apparatus 1, the light radiated by the light radiation unit 11 is the near infrared light. In this way, by using the near infrared light, which has higher transmissivity than visible light, it is possible to accurately inspect a condition of the article 50.

Figure 6:
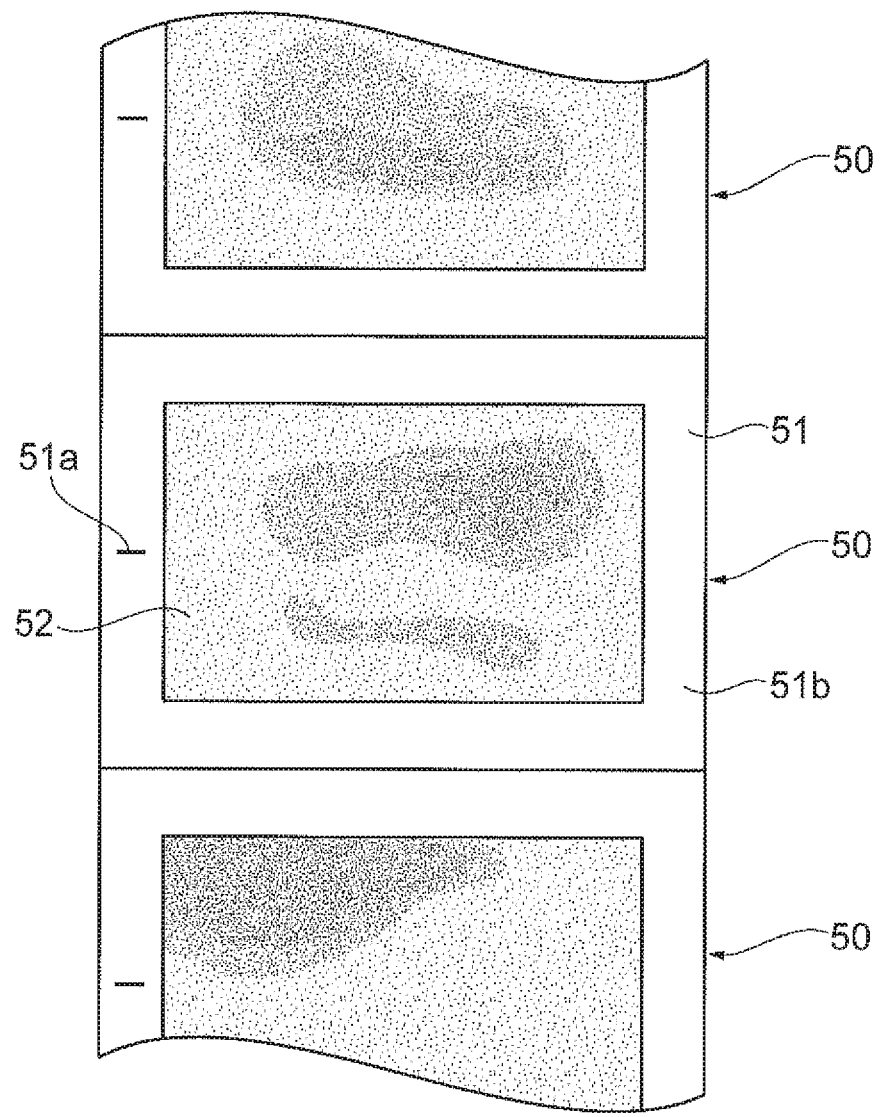
FIG. 6 is a plan view illustrating an article that is an object to be inspected by the optical inspection apparatus of FIG. 1.

Now, image processing performed by the control device (control unit) 30 is described herein. As illustrated in FIG. 6, the object to be inspected is the article 50 in which a seasoning for an instant food, for example, is packed as contents 52 in each of packages 51 of successive packaging (a plurality of connected small bags). The contents 52 caught in the sealed portion of the package 51 are inspected as described below. Note that such control device may also be provided in the optical inspection apparatus 1.

First, a light transmission image of the article 50 is acquired based on a detection signal output from the optical inspection apparatus 1. Next, a registration mark (mark) 51a is detected in the light transmission image of the article 50. Subsequently, based on a positional relationship of the sealed portion to the registration mark 51a saved in advance, an inspection region 51b corresponding to the sealed portion is set. Subsequently, by using the inspection region 51b as a target, the contents 52 caught in the sealed portion of the package 51 is inspected.

In this way, by using the registration mark 51a in which the attenuation of the light is large, it is possible to easily and securely set the sealed portion corresponding to the inspection region 51b. Note that by limiting the inspection region 51b by using mask processing or the like, it is possible to increase a processing speed. Note also that the package 51 is not limited to the successive packaging and may also be single packaging. Furthermore, it is also possible to set the inspection region 51b corresponding to the sealed portion based on a positional relationship between the sealed portion and an outer edge of the package 51 saved in advance without using the registration mark 51a.

One embodiment of the present invention has been described as above; however, the present invention is not to be limited to the above-described embodiment. For example, the light detection unit of the present invention is not limited to the line sensor and may also be an area sensor or the like. Furthermore, the light detection unit of the present invention may be provided with a filter that blocks light of a predetermined wavelength. For example, the light detection unit of the present invention may be provided with a filter that allows near infrared light to pass through while blocking visible light. Accordingly, in a case where the optical path of the near infrared light from the light radiation unit to the light detection unit is exposed to the ambient atmosphere, it is possible to prevent the visible light from entering the line sensor or the area sensor from the ambient atmosphere and becoming the ambient light. Furthermore, the light radiation unit of the present invention is not limited to one that radiates the near infrared light and may also be one that radiates visible light, ultraviolet light, infrared light, or the like. The light detection unit of the present invention may also be one that detects transmitted light of such light.

INDUSTRIAL APPLICABILITY

According to the present invention, it is possible to provide an optical inspection apparatus that can be easily installed in an existing conveying line conveying an article.

REFERENCE SIGNS LIST

1 . . . optical inspection apparatus, 11 . . . light radiation unit, 12 . . . light detection unit, 13 . . . support unit, 16 . . . pole unit, 17 . . . first beam unit, 17a . . . one end, 18 . . . second beam unit, 18a . . . one end, 30 . . . control device (control unit), 50 . . . article, 51 . . . package, 51b . . . inspection region, and 52 . . . contents.

The invention claimed is:

1. An optical inspection apparatus comprising:
a light radiation unit configured to radiate near infrared light to an article;
a light detection unit configured to detect transmitted light of the near infrared light radiated to the article; and
a support unit configured to support the light radiation unit and the light detection unit in a cantilever manner;
wherein an inspection region of the article by the near infrared light is exposed to an ambient atmosphere,
wherein the light radiation unit and the light detection unit are rotatable integrally with the support unit about a position as a center of rotation of the light radiation unit, the light detection unit, and the support unit, the position being at a shorter distance from the light radiation unit than a distance from the light detection unit, and
wherein the light radiation unit, the light detection unit, and the support unit are configured to be rotatable while being fixed with respect to each other.

2. The optical inspection apparatus according to claim 1, wherein the light detection unit is disposed upward relative to the light radiation unit.

3. The optical inspection apparatus according to claim 1, wherein the light radiation unit and the light detection unit are vertically movable integrally with the support unit.

4. The optical inspection apparatus according to claim 3, wherein a position of the light detection unit is adjustable relative to that of the light radiation unit.

5. The optical inspection apparatus according to claim 1, wherein the support unit includes:

a pole unit;
a first beam unit fixed to the pole unit at one end thereof and configured to support the light radiation unit; and
a second beam unit fixed to the pole unit at one end thereof and configured to support the light detection unit.

6. The optical inspection apparatus according to claim 1, further comprising a control unit configured to acquire a light transmission image of the article having contents contained in a package from the light detection unit, to set an inspection region corresponding to a sealed portion of the package based on a positional relationship of the sealed portion saved in advance, and to inspect the contents caught in the sealed portion with targeting the inspection region.

* * * * *